United States Patent
Li et al.

(10) Patent No.: US 12,121,320 B2
(45) Date of Patent: Oct. 22, 2024

(54) METHOD AND DEVICE FOR LABEL-FREE ALL-OPTICAL NEURAL REGULATION AND IMAGING

(71) Applicant: ZHEJIANG UNIVERSITY, Hangzhou (CN)

(72) Inventors: Peng Li, Hangzhou (CN); Lin Yao, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 439 days.

(21) Appl. No.: 17/771,457

(22) PCT Filed: Jul. 31, 2019

(86) PCT No.: PCT/CN2019/098679
§ 371 (c)(1),
(2) Date: Apr. 22, 2022

(87) PCT Pub. No.: WO2021/003782
PCT Pub. Date: Jan. 14, 2021

(65) Prior Publication Data
US 2022/0400955 A1    Dec. 22, 2022

(30) Foreign Application Priority Data
Jul. 9, 2019   (CN) .................. 201910614449.X (51) Int. Cl.
*A61B 5/00*   (2006.01)
*A61B 3/10*   (2006.01)
(Continued)

(52) U.S. Cl.
CPC ............ *A61B 5/0066* (2013.01); *A61B 3/102* (2013.01); *G01B 9/0209* (2013.01); *G01N 21/47* (2013.01)

(58) Field of Classification Search
CPC ....... A61B 5/0066; A61B 3/102; G01N 21/47
See application file for complete search history.

(56) References Cited

U.S. PATENT DOCUMENTS

| 6,549,795 B1 * | 4/2003 | Chance | A61B 5/14552 |
| | | | 600/340 |
| 9,232,896 B2 * | 1/2016 | Baym | A61B 5/0097 |

(Continued)

FOREIGN PATENT DOCUMENTS

| CN | 107788950 A | 3/2018 |
| CN | 108670192 A | 10/2018 |
| WO | 2009089509 A1 | 7/2009 |

OTHER PUBLICATIONS

Maheswari et al.; "Novel functional imaging technique from brain surface with optical coherence tomography enabling visualization of depth resolved functional structure in vivo", Journal of Neuroscience Methods 124 (2003) 83/92 (Year: 2003).*

(Continued)

*Primary Examiner* — Dixomara Vargas
(74) *Attorney, Agent, or Firm* — Bayramoglu Law Offices LLC (57) ABSTRACT

A method and a device for label-free all-optical neural regulation and imaging are provided. The method stimulates a neural activity through an infrared laser pulse, and acquires an optical scattered signal caused by the neural activity by optical coherence tomography (OCT) to realize label-free all-optical neural regulation and imaging. The method specifically includes: aiming an infrared laser at a target brain region, injecting a certain time series of laser pulses, synchronously scanning and imaging the target brain region by OCT, analyzing a relative change of an OCT scattered signal before and after laser stimulation, and acquiring a brain function signal based on OCT to realize synchronous neural regulation and imaging. The method and the device enable (Continued)

synchronous neural regulation and imaging without causing crosstalk between the regulation and imaging channels, and without the need for injection of a contrast agent or viral transfection.

14 Claims, 8 Drawing Sheets

(51) Int. Cl.
*G01B 9/0209* (2022.01)
*G01N 21/47* (2006.01)

(56) References Cited

U.S. PATENT DOCUMENTS

| | | | | |
|---|---|---|---|---|
| 10,568,516 | B2* | 2/2020 | Yang | A61B 5/4064 |
| 10,795,440 | B1* | 10/2020 | Chevillet | G06F 18/2413 |
| 11,813,476 | B1* | 11/2023 | Shanks | A61N 5/0622 |
| 2004/0064052 | A1* | 4/2004 | Chance | A61B 5/14553 |
| | | | | 600/476 |
| 2005/0107716 | A1* | 5/2005 | Eaton | A61B 5/0073 |
| | | | | 128/903 |
| 2005/0216072 | A1* | 9/2005 | Mahadevan-Jansen | |
| | | | | A61B 5/0048 |
| | | | | 607/89 |
| 2007/0100398 | A1* | 5/2007 | Sloan | A61N 1/36082 |
| | | | | 607/2 |
| 2007/0282189 | A1* | 12/2007 | Dan | A61B 5/0042 |
| | | | | 600/407 |
| 2008/0275340 | A1* | 11/2008 | Beach | A61B 8/0808 |
| | | | | 600/438 |
| 2010/0185256 | A1* | 7/2010 | Hulvershorn | A61N 1/361 |
| | | | | 607/45 |
| 2012/0215114 | A1* | 8/2012 | Gratton | A61B 5/02028 |
| | | | | 600/479 |
| 2013/0013030 | A1* | 1/2013 | Mahadevan-Jansen | |
| | | | | A61N 5/0622 |
| | | | | 607/89 |
| 2015/0078642 | A1* | 3/2015 | Fang | G06T 7/0012 |
| | | | | 382/131 |
| 2016/0015316 | A1* | 1/2016 | Borsook | A61B 5/14546 |
| | | | | 600/475 |
| 2017/0231501 | A1* | 8/2017 | Culver | A61B 5/0042 |
| | | | | 600/425 |
| 2017/0351958 | A1* | 12/2017 | Ghosh | G06N 5/04 |
| 2017/0365101 | A1* | 12/2017 | Samec | G06T 19/006 |
| 2018/0192931 | A1* | 7/2018 | Linden | A61B 5/14552 |
| 2018/0228375 | A1* | 8/2018 | Kim | G01N 33/582 |
| 2019/0150745 | A1* | 5/2019 | Sobek | A61B 5/0073 |
| 2019/0150751 | A1* | 5/2019 | Yang | H04N 23/45 |
| 2019/0183343 | A1* | 6/2019 | Yang | A61B 5/0035 |
| 2019/0269331 | A1* | 9/2019 | Alford | A61B 5/6803 |
| 2019/0336005 | A1* | 11/2019 | Alford | A61B 5/4064 |
| 2019/0336006 | A1* | 11/2019 | Horstmeyer | A61B 5/14552 |
| 2019/0336057 | A1* | 11/2019 | Alford | A61B 5/14553 |
| 2020/0022581 | A1* | 1/2020 | Vanegas | A61B 5/1118 |
| 2020/0113439 | A1* | 4/2020 | Mohseni | A61B 5/0042 |
| 2020/0114164 | A1* | 4/2020 | Bourke, Jr. | A61N 5/025 |
| 2020/0360721 | A1* | 11/2020 | Mohseni | A61N 5/0601 |
| 2022/0031224 | A1* | 2/2022 | Boctor | A61B 5/377 |

OTHER PUBLICATIONS

Akkin et al.; "Detection of neural action potentials using optical coherence tomography: intensity and phase measurements with and without dyes"; vol. 2—2010 (Year: 2010).*

Chen et al.; "Near-infrared deep brain stimulation via upconversion nanoparticle-mediated optogenetics"; vol. 359, No. 6376, pp. 679-684 (Year: 2018).*

Chernov et al.; "Infrared neural stimulation: a new stimulation tool for central nervous system applications"; Neurophotonics. Jul. 2014; 1(1): 011011; pp. 1-7 (Year: 2014).*

Pei; "3D optical imaging of microvascular net-works and its application on cerebral science"; Master thesis translation, pp. 1-62 (Year: 2019).*

Li Pei, 3D optical imaging of microvascular net-works and its application on cerebral science, Basic Sciences, China Master's Theses, 2018, pp. 1-62.

* cited by examiner

Pulsed near-infrared light stimulation timing

METHOD AND DEVICE FOR LABEL-FREE ALL-OPTICAL NEURAL REGULATION AND IMAGING

CROSS REFERENCE TO THE RELATED APPLICATIONS

This application is the national phase entry of International Application No. PCT/CN2019/098679, filed on Jul. 31, 2019, which is based upon and claims priority to Chinese Patent Application No. 201910614449.X, filed on Jul. 9, 2019, the entire contents of which are incorporated herein by reference.

TECHNICAL FIELD

The present disclosure belongs to the field of biomedical imaging, and relates to optical coherence tomography (OCT) and neural regulation, in particular to a method and device for label-free all-optical neural regulation and imaging based on low-coherence interferometry (LCI), which can be used in the fields of basic and applied neuroscience to study the response and mapping of cortical neurons under near-infrared (NIR) pulse stimulation.

BACKGROUND

The brain is the core of life activities, and the focus of scientists' research. When the brain is stimulated externally, it will produce changes in neural functional signals, which are closely related to biological functions. Therefore, the accurate analysis of changes in neural functional signals through neural regulation and imaging is of great significance for the study of human disease pathology.

For many brain function studies aimed at neural regulation and functional region tracking, neural stimulation is required to study functional responses of the brain. Electrical stimulation is a common tool for neural stimulation, but it is affected by current diffusion and often activates additional brain circuits, thereby leading to side effects. Besides, electrophysiological stimulation and signal recording are difficult to be performed synchronously due to stimulation artifacts. In contrast, optical stimulation has distinct advantages. Optogenetics is a specific cell stimulation technique that is compatible with electrical recording of animals under anesthesia and awake. However, the stimulation of primates requires virus injection. The time period of viral expression is relatively long, usually 4-6 weeks, and the stimulation site is limited to the site of viral expression. There are also other large-scale neural stimulation techniques (transcranial magnetic stimulation (TMS), ultrasound, etc.), but they have low spatial resolution.

Regarding neural signal recording, unit physiological recording is a common way for monitoring neural functions. However, its sampling is limited by the geometry of the electrode recording site and requires the electrode to be inserted into the brain. Regarding neural signal imaging, there are many imaging techniques available, each with its advantages and disadvantages. Among them, two-photon imaging can densely sample in the x, y and z-axes, and can reach cell-level resolution. However, it is limited by the sampling field of view and requires virus injection or gene transfection to label cells. Multi-photon imaging can reach depths of 1 mm or more, but it is not practical for large animal models. To monitor neural activity at the population level, the optical imaging technique by staining with a voltage sensitive dye (VSD) enables large-scale, high temporal resolution (1-10 ms) imaging. However, the correlation of tissue staining and photodynamic damage limits the application of VSD in large animals. Optical intrinsic signal imaging (OISI) based on hemodynamic signals is often used for larger-scale imaging without the addition of exogenous substances to the brain. OISI signals are highly correlated with neuronal population responses and can be used to map cortical columns, but OISI cannot achieve deep signal detection.

The above techniques can be combined to achieve neural stimulation and signal recording. However, the current methods need to be further improved to be non-contact (without inserting or applying any substance), large-scale (mm to cm scale), depth-resolved (to distinguish between different depths), and suitable for large animal models. Therefore, it is highly desirable to develop a method and device for synchronous neural regulation and imaging by an all-optical means to perform non-contact precise stimulation and signal detection synchronously.

SUMMARY

An objective of the present disclosure is to propose a method and device for label-free all-optical neural regulation and imaging. The present disclosure combines near-infrared (NIR) laser pulse stimulation and optical coherence tomography (OCT) and overcomes the deficiencies of the prior art.

The present disclosure regulates and maps brain nerve functions in a non-contact, large-scale, and depth-resolved (up to 1 mm) manner in the cerebral cortex by a label-free all-optical means.

The objective of the present disclosure is achieved by the following technical solutions.

I. A method for label-free all-optical neural regulation and imaging includes:
 S1: stimulating a neural activity through an infrared laser pulse:
 S2: synchronously acquiring, by OCT, an optical scattered signal caused by the neural activity; and
 S3: extracting a brain function signal through an OCT scattered signal.

The step of stimulating the neural activity through the infrared laser pulse includes: performing a single stimulation process, which includes three phases: a baseline period t0 without laser energy, a stimulation period t1 with laser energy and a recovery period t2 without laser energy, where the stimulation period t1 uses a 1870 nm laser, which has a pulse width of 250 μs, a pulse frequency of 200 Hz, and provides a total of 100 pulse sequences; and repeating the laser stimulation process (t0+t1+t2) for multiple times to improve signal stability.

The step of stimulating the neural activity through the infrared laser pulse includes: realizing a specific laser pulse width and frequency by using a chopper, current or voltage trigger control.

The step of synchronously acquiring, by the OCT, the optical scattered signal caused by the neural activity of a biological tissue includes: synchronously acquiring an infrared laser stimulation process and an OCT recording process by using external trigger control or a clock signal.

The step of synchronously acquiring, by the OCT, the optical scattered signal caused by the neural activity includes: performing, by the OCT, repeated scan imaging on a scattered signal sample of a biological tissue in a two-dimensional (2D) or three-dimensional (3D) space, where the repeated scan imaging is performed at a same spatial position for a time equivalent to a complete laser stimulation process t0+t1+t2, where the OCT imaging is realized by one selected from the group consisting of a time-domain OCT (TD-OCT) imaging technique, which changes an optical path of a reference arm by scanning, a spectral-domain OCT (SD-OCT) imaging technique, which records a spectral interference signal by a spectrometer, and a swept-source OCT (SS-OCT) imaging technique, which records the spectral interference signal by a swept light source.

The biological tissue can be a cerebral cortex, etc.

The step of extracting the brain function signal through the OCT scattered signal includes: extracting a neural response signal in a non-vascular region through the OCT scattered signal: processing the OCT scattered signal to acquire an OCT angiogram, and removing a position of a blood vessel in a space where an acquisition position is located from the OCT angiogram; calculating a relative change of the OCT scattered signal in comparison with the baseline period (t0); screening out continuously significantly changed signal points of the OCT scattered signal based on the baseline period (t0); processing, by the screened significantly changed signal points as a mask, the relative change of the OCT scattered signal to acquire functional OCT (fOCT) signals; and averaging the fOCT signals in an entire test process to reduce noise.

The step of extracting the brain function signal through the OCT scattered signal includes: extracting, by OCT angiography (OCTA), a blood flow signal change in a vascular region during a stimulation process.

There is a certain difference between a working wavelength of the NIR laser stimulation and a central wavelength of an OCT system, which ensures that the two optical channels of stimulation and imaging do not interfere with each other. The NIR laser stimulation adopts a 1870 nm laser, and the OCT imaging adopts a 1300 nm laser.

II. A device for label-free all-optical neural regulation and imaging includes:

an NIR laser stimulation device, configured to stimulate a neural activity of a target brain tissue;

an OCT detection device, configured to acquire an optical scattered signal in a 2D or 3D space;

a synchronization control unit, connected to the NIR laser stimulation device and the OCT detection device, and configured to synchronize a laser stimulation process and an OCT recording process; and one or more processors, connected to the NIR laser stimulation device and the OCT detection device, and configured to analyze and process the acquired OCT scattered signal.

The NIR laser stimulation device is provided with a working wavelength different from a central wavelength of the OCT system; the NIR laser stimulation device adopts a 1870 nm laser, and the OCT detection device adopts a 1300 nm laser.

The OCT detection device includes:

a low-coherence light source, an interferometer and a detector;

a low-coherence light source, an interferometer and a spectrometer; or a swept broadband light source, an interferometer and a detector.

The one or more processors are configured to calculate a change of a neural scattered signal in a non-vascular region and a change of a blood flow signal in a vascular region before and after laser stimulation to acquire brain function information.

Compared with the prior art, the present disclosure has the following beneficial effects:

Combining NIR laser pulse stimulation and OCT technology, the present disclosure stimulates the neural activity through infrared laser pulses and at the same time acquires optical scattered signal caused by the neural activity by OCT. In addition, the present disclosure extracts the brain function signal through the OCT scattered signal.

In the existing combination of optogenetic stimulation and optical calcium imaging, the optogenetic probe and the calcium indicator spectrally overlap, resulting in crosstalk between the stimulation and imaging channels. In contrast, the present disclosure maintains a certain difference between the working wavelength (1870 nm) of NIR laser stimulation and the central wavelength (1300 nm) of the OCT system, such that the two optical channels of stimulation and imaging do not interfere with each other.

In the existing combination of optogenetic stimulation and optical calcium imaging, there is strong visible light scattering within the tissue, resulting in limited stimulation and imaging depth. In contrast, the present disclosure designs both the stimulation and imaging channels to work in the NIR bands with deeper penetration, up to 1 mm.

In the existing combination of optogenetic stimulation and optical calcium imaging, the test animal requires viral transfection, which is not suitable for non-human primates. In contrast, the present disclosure does not require injection of contrast agents or viral transfection, and it is suitable for non-human primate studies and human studies in clinical settings.

Reference Numerals: 1. stimulate a neural activity by an infrared laser pulse; 2. acquire an optical scattered signal caused by the neural activity, by optical coherence tomography (OCT); 3. calculate a relative change of the OCT scattered signal; 11. light source; 12. beam splitter; 13. reference arm collimating mirror; 14. high-reflectivity plane mirror; 15. sample arm collimating mirror; 16. scanning galvanometer; 17. objective lens; 18. sample to be tested; 19. interference signal detection device; 20. signal processor; 21. polarization controller; 31. low-coherence broadband light source; 32. optical circulator; 33. fiber coupler; 34. first fiber collimation device; 35. focusing lens; 36. high-reflectivity plane mirror; 37. second fiber collimation device; 38. scanning galvanometer; 39. focusing lens; 40. sample dispersion device; 41. third fiber collimation device; 42. grating; 43. Fourier transform lens; 44. high-speed line-scan camera; 45. signal processor module and calculation unit; 46. first polarization controller; 47. second polarization controller; 48. dispersion compensator; 49. focusing lens; 50. dichroic mirror; 51. scanning lens; 52. signal controller; 53. laser; and 54. laser stimulation fiber.

DETAILED DESCRIPTION OF THE EMBODIMENTS

The specific implementations of the present disclosure will be described in detail below with reference to the drawings, which constitute a part of the present disclosure. It should be noted that these descriptions and examples are exemplary only and should not be construed as limiting the scope of the present disclosure. The protection scope of the present disclosure is defined by the appended claims, and any modifications based on the claims of the present disclosure are within the protection scope of the present disclosure.

To facilitate understanding of the embodiments of the present disclosure, the operations are described as multiple discrete operations, but the order of description does not represent the order in which the operations are implemented.

In the description, the sample measurement space is denoted by three-dimensional (3D) coordinates x-y-z based on the spatial directions. Such description is provided only to facilitate discussion and is not intended to limit the application of the embodiments of the present disclosure. The depth direction z is the direction along the incident optical axis. The plane x-y is a plane perpendicular to the optical axis, where x and y are orthogonal, and x denotes the transverse fast scan direction of optical coherence tomography (OCT), and y denotes the slow scan direction thereof.

i, I, t, etc. denote variables, which are only used to facilitate discussion and are not intended to limit the application of the embodiments of the present disclosure, and may be any numerical values such as 1, 2, and 3.

Figure 1:
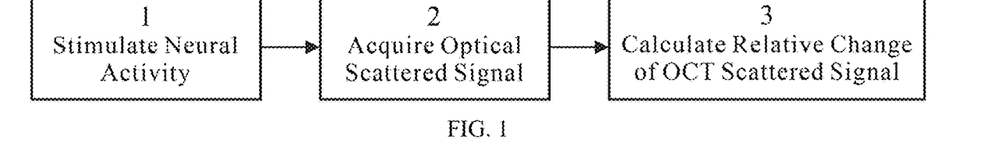
FIG. 1 is a schematic diagram of a method according to the present disclosure.

The method of the present disclosure is shown in FIG. 1. First, a target brain neural activity is stimulated by near-infrared (NIR) pulse stimulation. Then, a change in a scattered signal caused by the neural activity is acquired by an OCT system. Finally, a brain function signal is extracted through the OCT scattered signal.

The NIR pulse stimulation process includes three phases: a baseline period t0 without laser energy, a stimulation period t1 with laser energy and a recovery period t2 without laser energy. The stimulation period t1 uses a 1870 nm laser, which has a pulse width of 250 µs, a pulse frequency of 200 Hz, and provides a total of 100 pulse sequences. The laser stimulation process t0+t1+t2 is repeated for a plurality of times to improve signal stability.

Based on the change of the scattered signal caused by the neural activity acquired by the OCT system, OCT scanning imaging is performed on the scattered signal sample in a two-dimensional (2D) or 3D space. Repeated scan imaging is performed at the same spatial position for a certain time (total time t0+t1+t2). The imaging uses a time-domain OCT (TD-OCT) imaging technique, which changes an optical path of a reference arm by scanning; a spectral-domain OCT (SD-OCT) imaging technique, which records a spectral interference signal by a spectrometer; or a swept-source OCT (SS-OCT) imaging technique, which records the spectral interference signal by a swept light source.

The brain function signal is extracted through the OCT scattered signal, and the change of the neural scattered signal in a non-vascular region and the change of a blood flow signal in a vascular region before and after laser stimulation are calculated to acquire brain function information. Based on an OCT angiography, the position of a blood vessel in the space is removed so as to eliminate the influence of blood flow. In the data processing part, based on the scattered signal before stimulation (t0), the relative change of the OCT scattered signal during laser stimulation (t1) is calculated. Specifically, a baseline value of the OCT scattered signal is determined, where I(z, x, t) denotes an OCT intensity signal, which is an absolute value of the OCT scattered signal; z denotes a depth direction; x denotes a lateral direction; and t denotes a time dimension.

A blank time before stimulation is segment t0. The OCT scattered signal at the blank time is averaged to acquire the baseline value $I_{Baseline}$ of the OCT scattered signal before stimulation:

$$I_{Baseline} = \frac{1}{N}\sum_{i=1}^{N} I(z, x, t_i) \quad (1)$$

where N denotes a number of frames acquired during the time.

dR/R denotes a relative change of the OCT scattered signal acquired in real time compared to the baseline value of the OCT scattered signal:

$$dR/R(z, x, t) = \frac{I(z, x, t) - I_{Baseline}}{I_{Baseline}} \quad (2)$$

In order to improve the calculation efficiency, not all signal points at all times are used for calculation. However, they need to be screened according to certain principles. Specifically, if the OCT intensity signal intensity value of a pixel at a $(z, x, t_i)$ position is less than a value after subtracting $3\sigma(z, x)$ from $I_{Baseline}$ in 5 consecutive frames, this pixel is defined as a negative valid signal pixel:

$$I(z,x,t_i:t_{i+4}) < I_{Baseline} - 3\sigma(z,x) \quad (3)$$

where $3\sigma(z, x)$ denotes a standard deviation of all pixels at the (z, x) position.

Similarly, if the signal intensity value of the pixel at the position$(z, x, t_i)$ is greater than the value $I_{Baseline}$ plus $3\sigma(z,x)$ in 5 consecutive frames, then this pixel is defined as a positive valid signal pixel:

$$I(z,x,t_i:t_{i+4}) > I_{Baseline} + 3\sigma(z,x) \quad (4)$$

In this way, positive valid signal pixels and negative valid signal pixels are screened out, a mask is generated, and an fOCT signal is acquired. In the OCT scattered signal, the response value of the negative valid signal pixel is inverted and then together with the response value of the positive valid signal pixel, and the final fOCT signal is generated by averaging. This reduces noise and improves the signal-to-noise ratio (SNR).

Through an OCT angiography (OCTA), a hemodynamic response signal in the removed vascular region during the stimulation process is extracted, and the brain function signal is acquired by synthesizing the neural responses.

Figure 2:
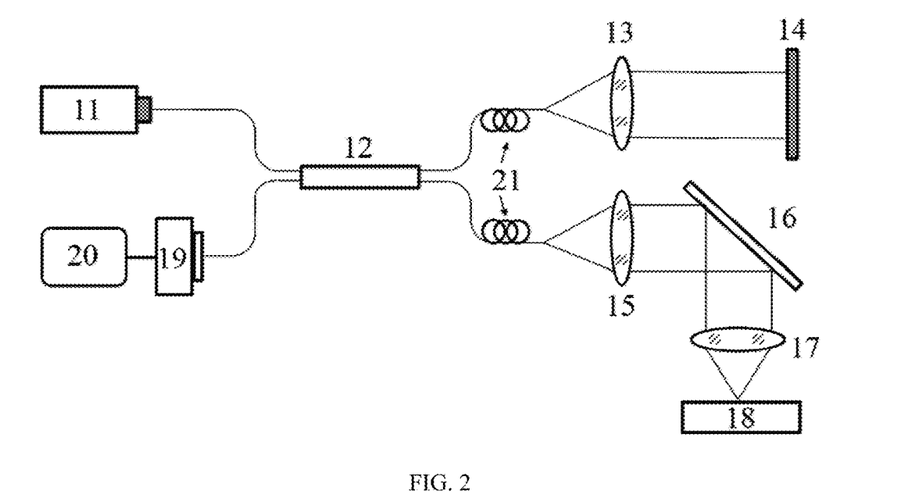
FIG. 2 is a schematic diagram of a device according to the present disclosure.

FIG. 2 is a schematic diagram of a device for label-free all-optical neural regulation and imaging according to the present disclosure. The main structure of a low-coherence interferometric measurement part of the device is an interferometer, which is composed of components denoted by 11 to 17, 19 and 21. The light emitted by a light source 11 is split into two beams by a beam splitter 12. One of the two beams enters a reference arm of the interferometer, and is irradiated on a high-reflectivity plane mirror 14 through a reference arm collimating mirror 13. The other of the two beams enters a sample arm, and is focused on a sample to be tested after being reflected by a sample arm collimating mirror 15 and an optical path. The sample 18 is placed at a focal plane of a sample arm objective lens 17. The light reflected from the reference arm and the sample arm interferes and is received by an interference signal detection device 19. For an optical fiber type optical path, a polarization controller 21 is used to adjust the polarization state of the beam so as to maximize the signal interference effect.

According to different ways of detecting signals by low coherence interference, the label-free all-optical neural regulation and imaging device shown in FIG. 2 specifically includes:

1) Time-domain measurement device. The light source 11 adopts low-coherence broadband light, the plane mirror 14 can move along the direction of an optical axis, and the interference signal detection device 19 is a point detector. The optical path of the reference arm is changed by moving the plane mirror 14. The interference signals of the two arms are detected by the point detector 19. Through the low-coherence interferometric detection of scattered signals in the z-direction of a certain spatial depth, the sampling volume of a depth-space dimension is acquired.

2) Spectral-domain measurement device. The light source 11 adopts low-coherence broadband light, the plane mirror 14 is fixed, and the interference signal detection device 19 adopts a spectrometer. The interference signal passes through a line-scan camera in the spectrometer, while the interference spectrum is recorded. The interference spectral signal is analyzed by a Fourier analysis method, and the scattered information in the depth z direction is acquired in parallel to acquire the sampling volume of the depth dimension space.

3) Sweep-frequency measurement device. The light source 11 adopts a swept light source, the plane mirror 14 is fixed, and the interference signal detection device 19 adopts a point detector. The point detector time-divisionally records the low-coherence interference spectrum of the swept light source. Through Fourier analysis of the interference spectral signal, the scattered information in the depth z direction is acquired in parallel to acquire the sampling volume of the depth dimension space.

The above different measurement devices can be combined with the OCT imaging method shown in FIG. 1 to analyze the relative motion of blood flow and surrounding tissue to generate an OCT angiogram and enhance the spatial correspondence.

Figure 3:
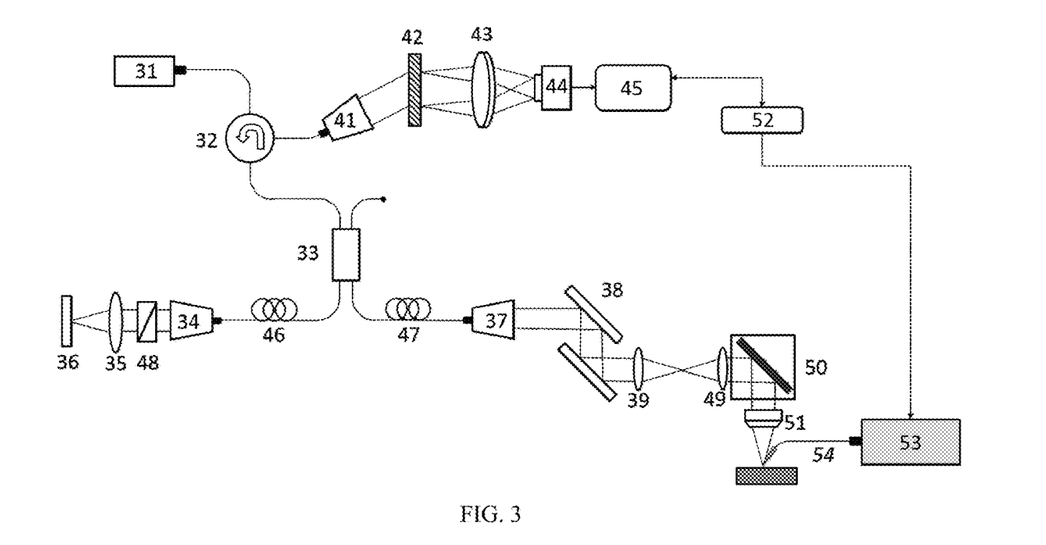
FIG. 3 is a schematic diagram of an embodiment of the present disclosure.

FIG. 3 is a schematic diagram of an exemplary embodiment of the present disclosure. It includes a low-coherence broadband light source 31, an optical circulator 32, a fiber coupler 33 with a splitting ratio of 50:50, a first polarization controller 46, a first fiber collimation device 34, a focusing lens 35, a high-reflectivity plane mirror 36, a second polarization controller 47, a second fiber collimation device 37, a scanning galvanometer 38, an objective lens 39, a sample dispersion device 40, a third fiber collimation device 41, a grating 42, a Fourier transform lens 43, a high-speed line-scan camera 44, a signal processor module and calculation unit 45, a dispersion compensator 48, a focusing lens 49, a dichroic mirror 50, a scanning lens 51, a signal controller 52, a laser 53 and a laser stimulation fiber 54. The signal controller 52 adopts a Cygnus Technology PG4000A digital controller. The laser 53 is a fiber-coupled semiconductor laser with an operating band of 1870 nm. The low-coherence broadband light source 31 adopts a super light-emitting diode (LED) light source with a central wavelength of 1,325 nm and a bandwidth of 100 nm. The high-speed line-scan camera 44 employs a line-scan camera composed of 2,048-pixel units. The scanning lens 51 in the sample arm is a lens with a focal length of 36 mm.

The laser 53 emits NIR laser light, and irradiates the sample to be tested through the laser stimulation fiber 54. The light emitted by the low-coherence broadband light source 31 used in the device of the present disclosure passes through the optical circulator 32 and then enters the fiber coupler 33 with a splitting ratio of 50:50. The light exiting from the fiber coupler 33 is split into two beams. One of the two beams passes through the optical fiber and is connected to the first fiber collimation device 34 in the reference arm via the first polarization controller 46. After collimation, dispersion compensation by the dispersion compensator 48 and focusing by the focusing lens 35, it is irradiated to the high-reflectivity plane mirror 36. The other of the two beams passes through the optical fiber and is connected to the second fiber collimation device 37 of the sample arm via the second polarization controller 47. It is irradiated onto the sample to be tested after being collimated, reflected by the optical path of the scanning galvanometer 38, and focused by the focusing lens 39 and the focusing lens 49. The dichroic mirror 50 located in front of the scanning lens 51 turns the OCT detection optical path formed by the light emitted from the focusing lens 49 by 90°. The scanning galvanometer 38 in the sample arm is fixed, such that the low-coherence interferometer can detect the scattered signals in the depth direction at the same position in the sample space at different times in parallel. Meanwhile, the optical path in the sample arm conducts the light beam through a single-mode fiber, and plays a role of spatial filtering the light scattered back by the sample to be tested to effectively reduce the multiple scattering components in the scattered signal. The light reflected by the high-reflectivity plane mirror 36 in the reference arm interferes at the fiber coupler 33 with the light backscattered by the sample to be tested in the sample arm. The interference light is detected and recorded by the spectrometer (including the components 41 to 44), and then collected by the signal controller 52 and the calculation unit 45 for signal analysis and processing. The optical stimulation unit and the OCT signal acquisition unit are synchronized by means of external trigger control and clock signal.

Figure 4:
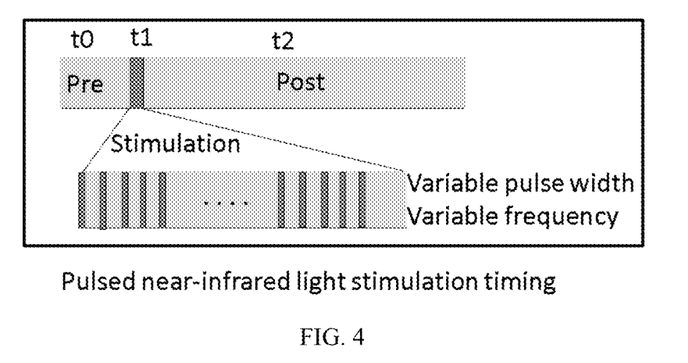
FIG. 4 is a sequence of near-infrared (NIR) laser stimulation according to an exemplary embodiment of the present disclosure.

In the present disclosure, neural responses and hemodynamic responses before and after stimulation and their characteristics are acquired from the fOCT signals. FIG. 4 shows a sequence of NIR laser stimulation. There is no laser energy in the t0 time period, the laser energy starts to work in the t1 time period, and the t2 time period is a recovery period without laser energy. The pulse width of each pulse in the output laser pulse sequence is adjustable, and the pulse period is adjustable. In a specific implementation, the fixed pulse width of each pulse is 250 μs, and the pulse period is 5 ms. The NIR laser stimulation includes 100 such pulses in a 0.5-s pulse link. The laser is output through a special optical fiber and irradiated to the target region of the optical observation window of a rat.

Figure 5A:
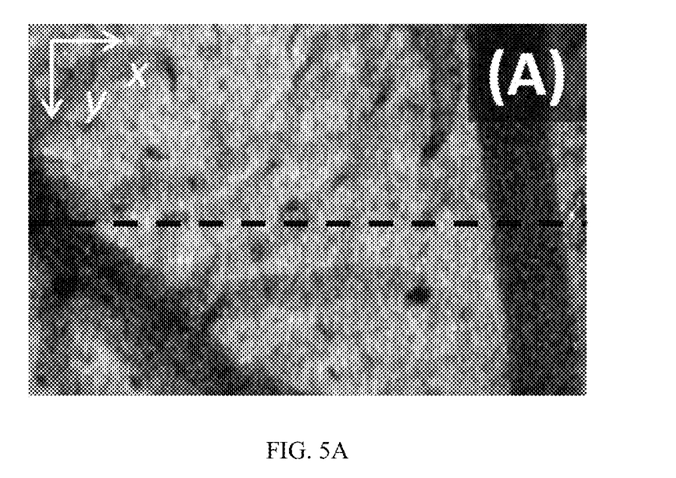
FIGS. 5A and 5B show a structure acquired by optical coherence tomography (OCT) according to an exemplary embodiment of the present disclosure.
Figure 5B:
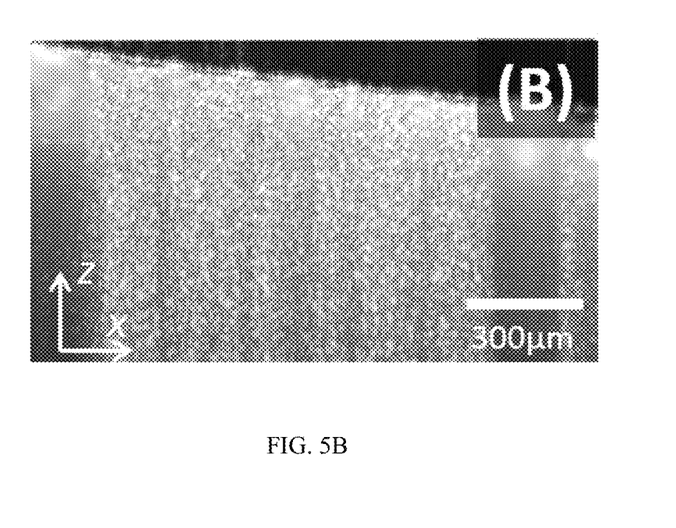

FIGS. 5A and 5B show a structure acquired by OCT, where OCT can realize 3D structure imaging. FIG. 5A is a projection view of the structure acquired by OCT, and FIG. 5B is a cross-sectional view along the dotted line in FIG. 5A.

Figure 6A:
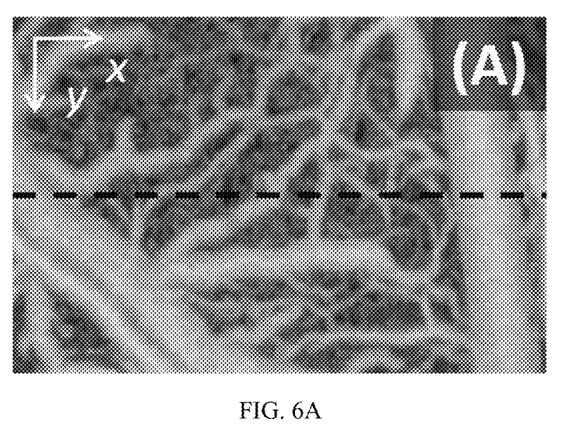
FIGS. 6A and 6B show an OCT angiogram according to an exemplary embodiment of the present disclosure.
Figure 6B:
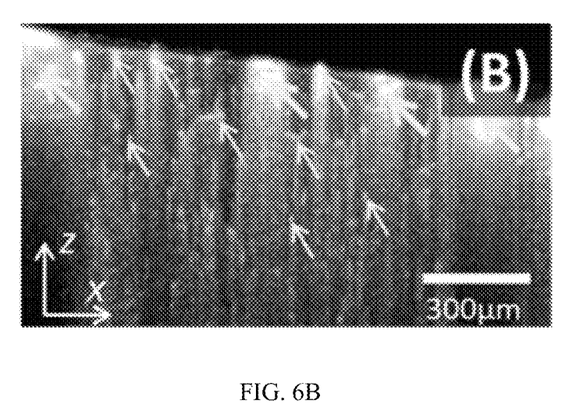

FIGS. 6A and 6B show an OCT angiogram. Through the OCT angiogram, a 3D blood flow signal can be acquired by processing a 3D structural signal acquired by OCT. FIG. 6A is a projection view of the OCT angiogram, and FIG. 6B is a cross-sectional view along the dotted line in FIG. 6A.

Figure 7:
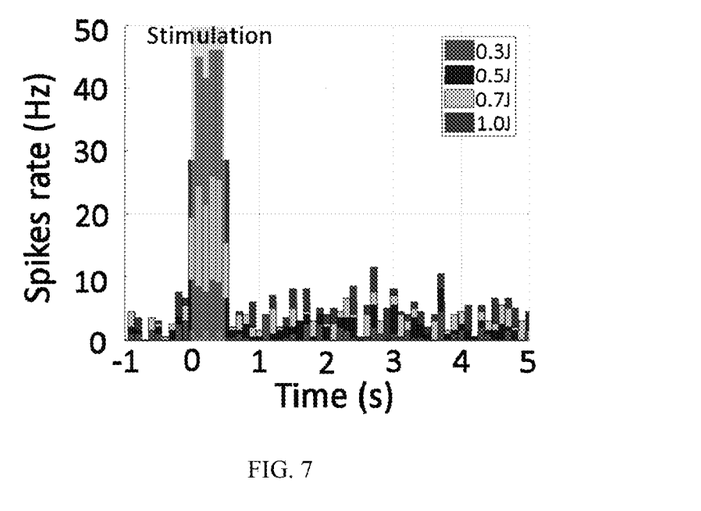
FIG. 7 is an electrophysiological signal diagram according to an exemplary embodiment of the present disclosure.

FIG. 7 shows the results of electrophysiological signals under different stimulation intensities (0.3 J, 0.5 J, 0.7 J, 1.0 J/cm$^2$/pulse). As the intensity of NIR laser stimulation increases, the spike rate increases. This indicates that the NIR laser stimulation of the trunk motor-sensory cortex of the rat can cause a neuronal stimulation activity Therefore, there may be a potential correlation between the subsequently observed changes in the fOCT response signal and the activity of neurons elicited by external stimuli.

FIGS. 8A to 11 show graphs of changes in the fOCT function signals of the cerebral cortex of the rat acquired in this embodiment. To characterize the fOCT signal evoked by the NIR laser stimulation, the present disclosure validates the temporal and spatial distribution of neural responses in the non-vascular region, their relationship to the stimulation intensity, and hemodynamic responses in the vascular region.

Figure 8A:
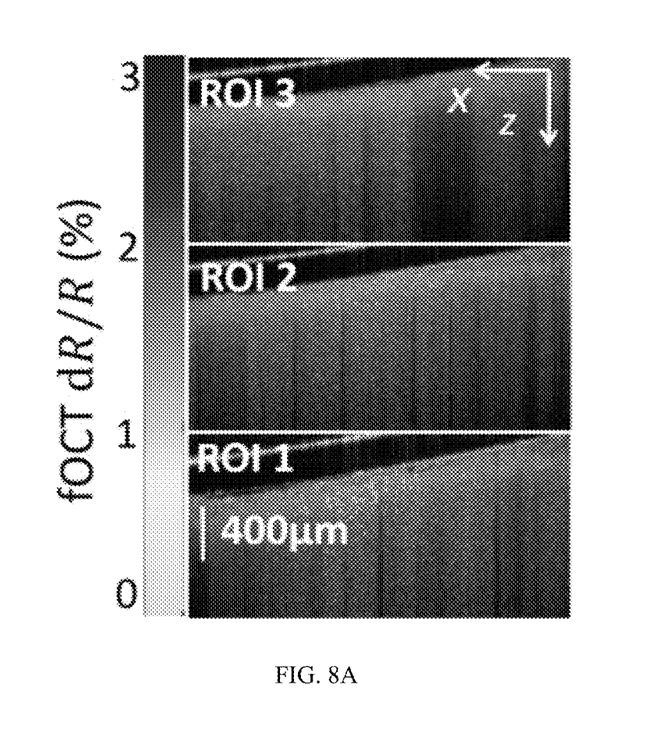
FIGS. 8A to 8C show a spatial distribution diagram of an fOCT signal according to an exemplary embodiment of the present disclosure.
Figure 8B:
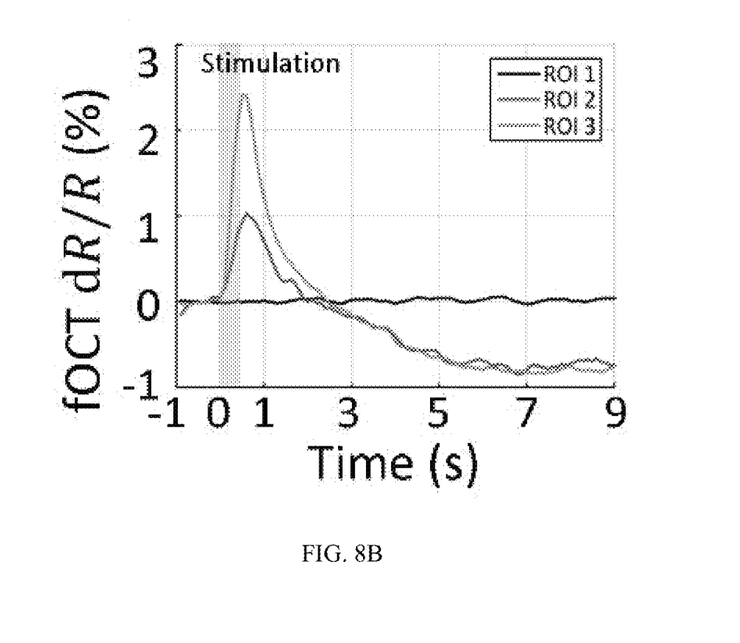
Figure 8C:
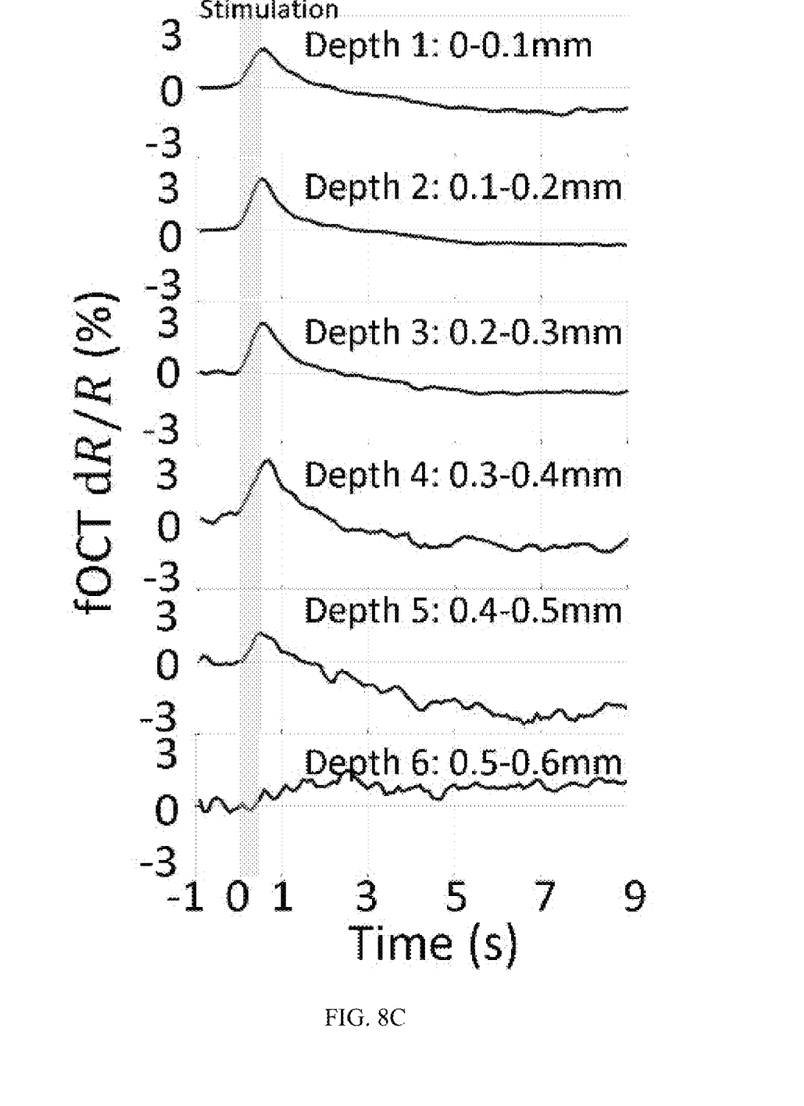

As shown in FIG. 8A, without moving the laser stimulation fiber and using the same stimulation parameters, the OCT system acquires signals from the center and surrounding of the NIR laser stimulation region, and observes the fOCT response (ROI1: center, ROI2: edge, ROI3: outer). The result graph shows that the NIR laser stimulation induces relative changes in the OCT scattered signal in the cerebral cortex of the rat (the signal changes in FIG. 8A are quantitatively analyzed in FIG. 8B). ROI1 includes the largest number of valid pixels (449 pixels); ROI2 includes a reduced number of valid pixels (354 pixels); and ROI3 shows no significant change in the scattered signal. In summary, the fOCT signal reflects the spatial localization of the neural signal (FIG. 8A) and the average amplitude of all valid pixels and the evoked fOCT signal over time (FIG. 8B). Further, as shown in the depth-resolved sequence in FIG. 8C, the temporal correspondence of the fOCT changes can be maintained to a depth range of 600 μm in the cortex.

Figure 9A:
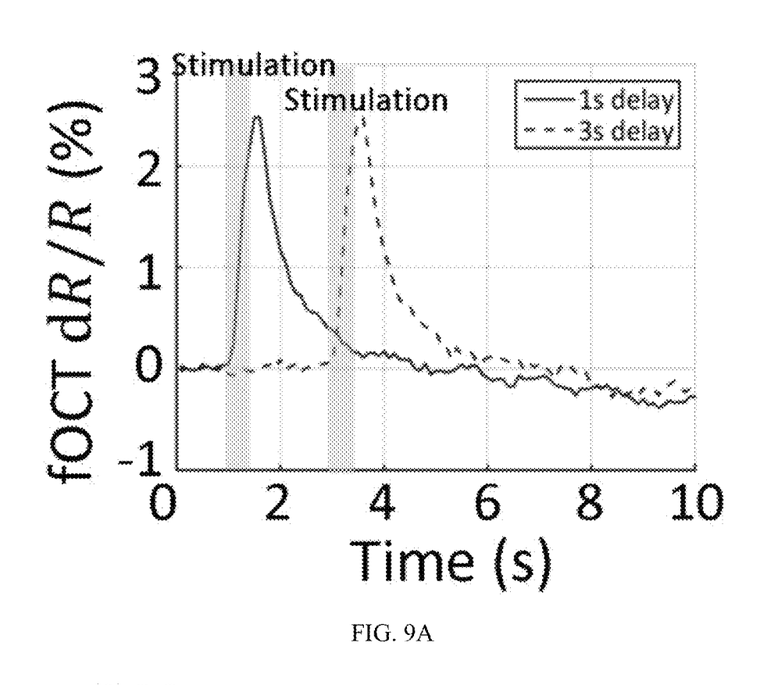
FIGS. 9A and 9B show a time distribution diagram of an fOCT signal according to an exemplary embodiment of the present disclosure.
Figure 9B:
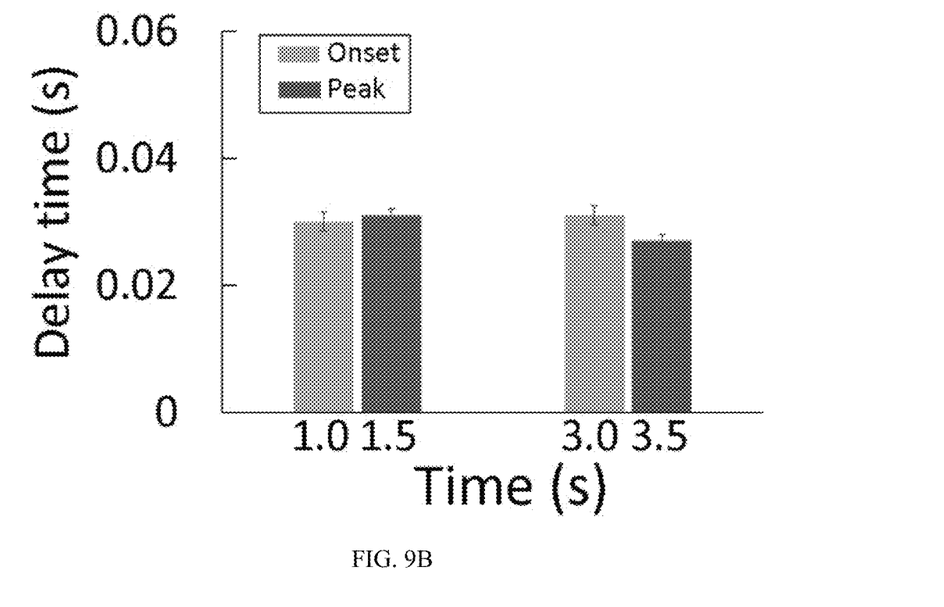

The fOCT signal is also temporally closely related to the NIR laser stimulation time. As shown in FIGS. 9A and 9B, the changes in the OCT scattered signal are synchronized with the NIR laser stimulation. All pixels with significant changes in the test are averaged for population responses. There is a similar temporal coincidence in the scattering changes in FIG. 9A. If the stimulation onset times are different, the response onset time and the response peak time are delayed, as shown in FIG. 9B. The results show that the fOCT response is temporally synchronized with the laser stimulation, with a time delay of approximately 30 ms.

Figure 10A:
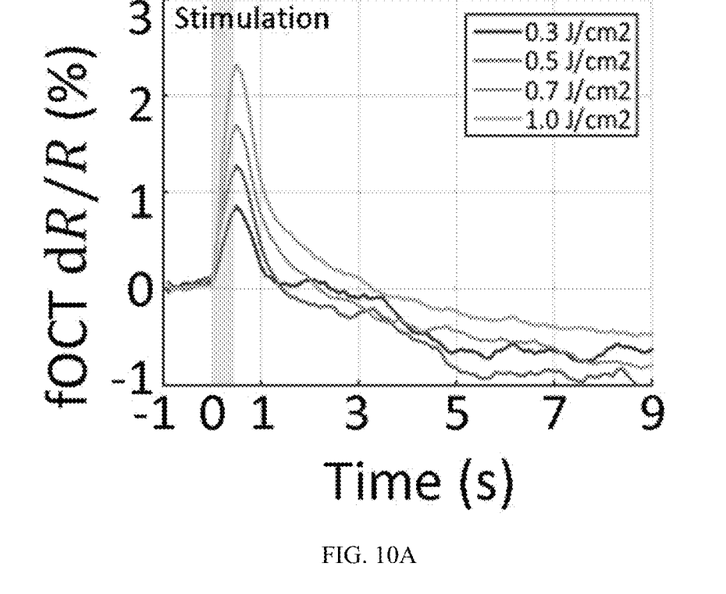
FIGS. 10A and 10B show a correlation diagram of the fOCT signal and a stimulation intensity according to an exemplary embodiment of the present disclosure.
Figure 10B:
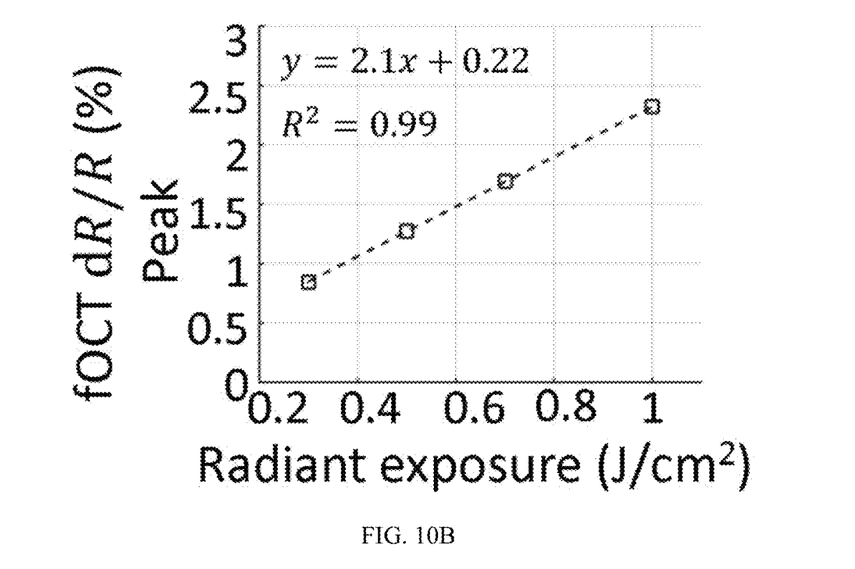

FIGS. 10A and 10B show functional responses at different stimulation intensities (0.3, 0.5, 0.7, 1.0 J/cm$^2$/pulse). Increasing the intensity of NIR laser stimulation will lead to an increase in the magnitude of the change of the fOCT signal, as shown in FIG. 10A. There is a linear relationship between the peak value of the change of the fOCT signal and the stimulation intensity, and the results are shown in FIG. 10B. Due to the high sensitivity of the interferometric detection, the magnitude of the change of the fOCT signal is large (slope of the linear fit: 2.1).

Figure 11:
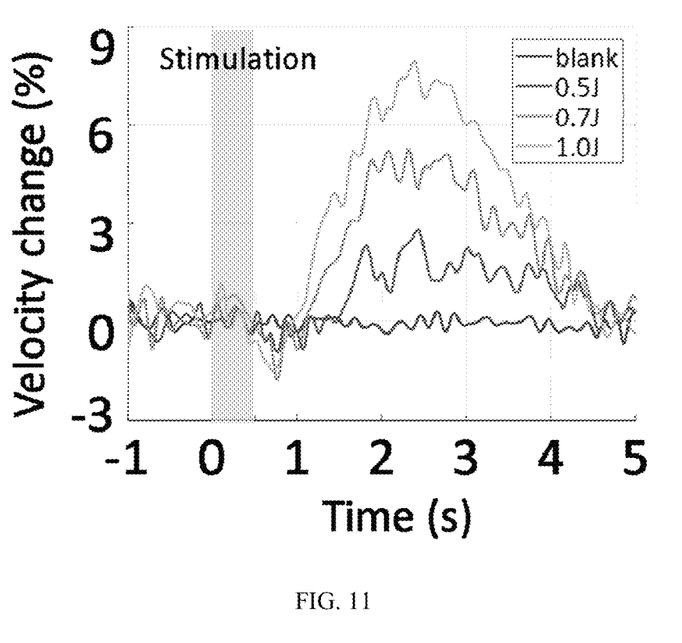
FIG. 11 shows a change in a blood flow velocity according to an exemplary embodiment of the present disclosure.

FIG. 11 shows the hemodynamic responses at different stimulation intensities (0.5, 0.7, 1.0 J/cm$^2$/pulse) with an increased OCT acquisition frequency. The increase in the intensity of NIR laser stimulation will also lead to an increase in the magnitude of the velocity change in the vascular region, and the time delay of the velocity change is about 1 s.

The above test results fully illustrate: the present disclosure enables synchronous neural regulation and imaging without crosstalk between the regulation and imaging channels, and injection of a contrast agent or viral transfection. In addition, the present disclosure can realize regulation and imaging of deep tissue regions through a near-infrared (NIR) waveband. The present disclosure can realize label-free all-optical neural regulation and imaging, and can synchronously perform non-contact precise stimulation and brain function signal detection in the target region.

What is claimed is:

1. A method for label-free all-optical neural regulation and imaging, comprising:
    stimulating a neural activity of a biological tissue through an infrared laser pulse, wherein the stimulating comprises:
        performing a single stimulation process, wherein the single stimulation process comprises three phases: a baseline period t0 without laser energy, a stimulation period t1 with laser energy and a recovery period t2 without laser energy, wherein
        in the stimulation period t1, an 1870 nm laser is applied on the biological tissue;
        the 1870 nm laser has a pulse width of 250 μs, a pulse frequency of 200 Hz, and provides a total of 100 pulse sequences; and
        repeating a laser stimulation process t0+t1+t2 for a plurality of times;
    synchronously acquiring, by optical coherence tomography (OCT), an optical scattered signal caused by the neural activity to obtain an OCT scattered signal by applying a 1300 nm laser to the biological tissue; and
    extracting a brain function signal through the OCT scattered signal; and
    generating an image of the brain function signal based on the extracting.

2. The method for label-free all-optical neural regulation and imaging according to claim 1, wherein the step of stimulating the neural activity through the infrared laser pulse comprises: realizing a specific laser pulse width and frequency by using a chopper, current or voltage trigger control.

3. The method for label-free all-optical neural regulation and imaging according to claim 1, wherein the step of synchronously acquiring, by the OCT, the optical scattered signal caused by the neural activity of the biological tissue comprises: synchronously acquiring an infrared laser stimulation process and an OCT recording process by using external trigger control or a clock signal.

4. The method for label-free all-optical neural regulation and imaging according to claim 1, wherein the step of synchronously acquiring, by the OCT, the optical scattered signal caused by the neural activity comprises: performing, by the OCT, repeated scan imaging on the biological tissue in a two-dimensional (2D) or three-dimensional (3D) space, wherein the repeated scan imaging is performed at a same spatial position for a time equivalent to a complete laser stimulation process t0+t1+t2, wherein an OCT imaging is realized by one selected from the group consisting of a time-domain OCT (TD-OCT) imaging technique, a spectral-domain OCT (SD-OCT) imaging technique and a swept-source OCT (SS-OCT) imaging technique, wherein the TD-OCT imaging technique changes an optical path of a reference arm by scanning, the SD-OCT imaging technique records a spectral interference signal by a spectrometer, and the SS-OCT imaging technique records the spectral interference signal by a swept light source.

5. The method for label-free all-optical neural regulation and imaging according to claim 1, wherein the step of extracting the brain function signal through the OCT scattered signal comprises: extracting a neural response signal in a non-vascular region through the OCT scattered signal:

processing the OCT scattered signal to acquire an OCT angiogram, and removing a position of a blood vessel in a space from the OCT angiogram, wherein an acquisition position is located in the space;

calculating a relative change of the OCT scattered signal in comparison with the baseline period t0;

screening out continuously significantly changed signal points of the OCT scattered signal based on the baseline period t0;

processing, by the continuously significantly changed signal points as a mask, the relative change of the OCT scattered signal to acquire functional OCT (fOCT) signals; and averaging the fOCT signals in an entire test process to reduce noise.

6. The method for label-free all-optical neural regulation and imaging according to claim 1, wherein the step of extracting the brain function signal through the OCT scattered signal comprises: extracting, by OCT angiography (OCTA), a blood flow signal change in a vascular region during a stimulation process.

7. A device for label-free all-optical neural regulation and imaging, comprising:

a near-infrared (NIR) laser stimulation device, configured to stimulate a neural activity of a target brain tissue by performing a single stimulation process, wherein the single stimulation process comprises three phases: a baseline period t0 without laser energy, a stimulation period t1 with laser energy and a recovery period t2 without laser energy, wherein in the stimulation period t1, an 1870 nm laser is applied on the target brain tissue;

the 1870 nm laser has a pulse width of 250 µs, a pulse frequency of 200 Hz, and provides a total of 100 pulse sequences; and repeating a laser stimulation process t0+t1+t2 for a plurality of times;

an optical coherence tomography (OCT) detection device, configured to acquire an optical scattered signal in a two-dimensional (2D) or three-dimensional (3D) a 2D er 3D-space by applying a 1300 nm laser to the target brain tissue;

a synchronization control unit, connected to the NIR laser stimulation device and the OCT detection device, and configured to synchronize a laser stimulation process and an OCT recording process; and one or more processors, connected to the NIR laser stimulation device and the OCT detection device, and configured to analyze and process the OCT scattered signal and generate an image of a brain function signal based on the OCT scattered signal.

8. The device for label-free all-optical neural regulation and imaging according to claim 7, wherein the NIR laser stimulation device is provided with a working wavelength different from a central wavelength of the OCT detection device.

9. The device for label-free all-optical neural regulation and imaging according to claim 7, wherein the one or more processors are configured to calculate a change of a neural scattered signal in a non-vascular region and a change of a blood flow signal in a vascular region before and after laser stimulation to acquire brain function information.

10. The device for label-free all-optical neural regulation and imaging according to claim 7, wherein the NIR laser stimulation device is configured to stimulate the neural activity by realizing a specific laser pulse width and frequency by using a chopper, current or voltage trigger control.

11. The device for label-free all-optical neural regulation and imaging according to claim 7, wherein the OCT detection device is configured to acquire the optical scattered signal by synchronously acquiring an infrared laser stimulation process and an OCT recording process by using external trigger control or a clock signal.

12. The device for label-free all-optical neural regulation and imaging according to claim 7, wherein the OCT detection device is configured to acquire the optical scattered signal by: performing, by the OCT, repeated scan imaging on the target brain tissue in the 2D or 3D space, wherein the repeated scan imaging is performed at a same spatial position for a time equivalent to a complete laser stimulation process t0+t1+t2, wherein an OCT imaging is realized by one selected from the group consisting of a time-domain OCT (TD-OCT) imaging technique, a spectral-domain OCT (SD-OCT) imaging technique and a swept-source OCT (SS-OCT) imaging technique, wherein the TD-OCT imaging technique changes an optical path of a reference arm by scanning, the SD-OCT imaging technique records a spectral interference signal by a spectrometer, and the SS-OCT imaging technique records the spectral interference signal by a swept light source.

13. The device for label-free all-optical neural regulation and imaging according to claim 7, wherein the one or more processors is configured to extract the brain function signal through the OCT scattered signal comprises: by extracting a neural response signal in a non-vascular region through the OCT scattered signal by:

processing the OCT scattered signal to acquire an OCT angiogram, and removing a position of a blood vessel in a space from the OCT angiogram, wherein an acquisition position is located in the space;

calculating a relative change of the OCT scattered signal in comparison with the baseline period t0;

screening out continuously significantly changed signal points of the OCT scattered signal based on the baseline period t0;

processing, by the continuously significantly changed signal points as a mask, the relative change of the OCT scattered signal to acquire functional OCT (fOCT) signals; and averaging the fOCT signals in an entire test process to reduce noise.

14. The device for label-free all-optical neural regulation and imaging according to claim 7, wherein the one or more processors is configured to extract the brain function signal through the OCT scattered signal by extracting, by OCT angiography (OCTA), a blood flow signal change in a vascular region during a stimulation process.

* * * * *